United States Patent [19]

Banks

[11] Patent Number: 4,824,440
[45] Date of Patent: Apr. 25, 1989

[54] PRODUCTION OF METHANE CONTAINING GASES

[75] Inventor: Reginald G. S. Banks, West Midlands, United Kingdom

[73] Assignee: British Gas plc, London, United Kingdom

[21] Appl. No.: 20,901

[22] Filed: Mar. 2, 1987

[30] Foreign Application Priority Data

Mar. 21, 1986 [GB] United Kingdom ............... 8607029

[51] Int. Cl.$^4$ .............................. C10J 3/16; C07C 9/04
[52] U.S. Cl. ....................................... 48/206; 48/210; 48/214 A; 585/733
[58] Field of Search ................. 48/197 R, 214 A, 206, 48/210; 385/733

[56] References Cited

U.S. PATENT DOCUMENTS

| | | |
|---|---|---|
| 3,433,610 | 3/1969 | Feldkirchner et al. . |
| 3,926,584 | 12/1975 | Adsetts ............... 48/214 A |
| 4,105,591 | 8/1978 | Banks et al. ............ 48/214 A |
| 4,185,967 | 1/1980 | Komodromos et al. ......... 48/214 A |
| 4,400,182 | 8/1983 | Davies et al. . |
| 4,483,691 | 11/1984 | McShea et al. .................. 48/244 A |

FOREIGN PATENT DOCUMENTS

| | | | |
|---|---|---|---|
| 1474601 | 3/1967 | France ............................. | 48/214 A |
| 820257 | 9/1959 | United Kingdom . | |
| 981726 | 1/1965 | United Kingdom . | |
| 1029711 | 5/1966 | United Kingdom . | |
| 1183925 | 6/1967 | United Kingdom . | |
| 1094633 | 12/1967 | United Kingdom . | |
| 1189001 | 4/1970 | United Kingdom ............. | 48/214 A |
| 1219461 | 1/1971 | United Kingdom . | |
| 1265481 | 3/1972 | United Kingdom . | |

OTHER PUBLICATIONS

Kirk-Othmer, Encyclopedia of Chemical Technology, Third Edition, Vol. 17, pp. 126–128, 188, 216, 218, 1982.

*Primary Examiner*—Peter Kratz
*Attorney, Agent, or Firm*—Larson and Taylor

[57] ABSTRACT

Heterocyclic and O-substituted aromatic species, for example those obtained as a by product of coal gasification, may be gasified by reaction with steam in the presence of a nickel-alumina containing catalyst to produce methane-containing gases. The reforming reaction is carried out at temperatures of not greater than 500° C.

2 Claims, No Drawings

PRODUCTION OF METHANE CONTAINING GASES

This invention relates to the production of methane-containing gases, more particularly to the production of methane-containing gases suitable for the production of substitute natural gas (SNG) by catalytic steam reforming processes.

Substitute natural gas is currently required to augment supplies of natural gas, particularly at times of peak load. As supplies of natural gas become exhausted, SNG production will become a base load operation and currently there are many avenues of research to find efficient and cost effective ways for producing methane-containing gases as the precursor to SNG.

One highly researched route is the gasification of coal. Current techniques are based upon the non-catalytic partial-oxidation of the solid coal feed with steam and oxygen. As a by-product of such coal gasification processes a tarry liquor condensate is produced which contains polynuclear, heterocyclic and substituted aromatic species e.g. phenols.

This by-product is a pullutant and, in any event is difficult to handle. However, it does represent a useful source of energy and proposals for recovering this energy have included recycling the liquor as a feedstock for the main gasification process or burning the condensate to provide process heat for the main gasification process.

We have now found that the liquor can be advantageously utilized as a source for feedstock for a catalytic peak load process such as CRG Process originally described in UK patent specification No. 820257, if the liquor is first distilled or fractionated to obtain volatile or vaporisable components. The fraction product still contains compounds of sulphur and oxygen, and although the feedstock would have to be purified to remove sulphur compounds, which are known catalyst poisons, we have unexpectedly found that it is not necessary to remove oxygen-containing compounds even though it would be expected that they would deactivate catalysts.

Accordingly, the present invention provides a process for the production of methane-containing gases wherein an aromatic feedstock is reacted with steam—preferably in a ratio of 3 parts steam to 1 part feedstock—in the presence of a nickel-alumina containing coprecipitated catalyst characterised in that the aromatic feedstock is a heterocyclic or O-substituted aromatic compound and that said reaction is effected at a temperature of not greater than 500° C.

The feedstocks for the process of this invention are mixtures of aromatic hydrocarbons including heterocyclic species and/or other oxygen containing derivatives. The feedstock should be vaporisable at temperatures of not more than 500° C. and may be obtained by the fractionation of coal liquors or condensates obtained by the gasification of coal.

The catalyst employed in the process of the invention may be any co-precipitated nickel-alumina catalyst used for steam reforming hydrocarbons. Such catalysts are disclosed for example in UK patent specification Nos. 1525017 and 1550749 and in European patent publication No. 0010114.

A typical feedstock specification would have a boiling range of 80°–270° C. and a mean molecular weight of about 103. The ratio of oxygen to carbon is preferably about 0.01:1 by weight.

Although it might be expected that high inlet temperatures e.g. of the order of 550° C. or higher would be required to gasify the relatively high molecular weight species, we have found that the use of such temperatures confers no advantage. In fact catalyst performance is deleteriously effected and we have suprisingly found that temperatures of not greater than 500° C. are required. It is normally necessary to employ any recycle of the produce gas.

The invention will be described in further detail with reference to the following Example.

EXAMPLE 1

About 16 gm of 3.2×3.2 mm cylindrical pellets of a nickel-chromia-alumnina catalyst, prepared in accordence with Example 3 (Catalyst I) of UK patent specification No. 1550749 was loaded into a reactor tube of 4.5 mm internal diameter. The catalyst was reduced in hydrogen at 550° C. for 16 hours.

In a first (Control) reaction, a feedstock comprising benzene (25 parts per hundred by volume), toluene (25 pph), xylene (25 pph), tetrahydronaphthalene (15 pph) and decahydronaphthalene (10 pph) was passed through the reactor tube at a rate of 39 ghr$^{-1}$. Steam at a rate of 118 ghr$^{-1}$ and hydrogen at a rate of 9.7 lhr$^{-1}$ was passed in simultaneously with the feedstock. The inlet temperature was 550° C. and the pressure was 45 bar. The test was continued for a period of 940 hours when aromatic hydrocarbons were detected in the outlet gas from the reactor.

A second test was then conducted under the same conditions as described for the first test except that the feedstock contained, in addition, 50 g liter$^{-1}$ of phenol. The test lasted for only 438 hours when the catalyst bed became blocked. Examination of the catalyst showed that the blockage was caused by carbon deposited on the catalyst, mainly at the bed inlet.

A third test was then carried out under similar conditions to that of the second test except that an inlet temperature of 500° C. was used. The test lasted for 1012 hours during which time no blockage of the catalyst bed occured and no aromatic hydrocarbons were detected at the bed outlet.

I claim:

1. A process for the production of methane-containing gases wherein an aromatic feedstock is reacted with steam in the presence of a nickel-alumina-containing coprecipitated catalyst, said aromatic feedstock being vaporizable at a temperature of not more than 500° C., being obtained by removing sulfur-containing compounds from a fraction obtained by distillation or fractionation of a tarry liquor condensate produced as a by-product of coal gasification, said feedstock containing heterocyclic oxygen-containing aromatic compounds or oxygen-substituted aromatic compounds, or both, said reaction being effected at a temperature of not greater than 500° C.

2. A process according to claim 1 wherein said coal gasification is effected via non-catalytic partial-oxidation of solid coal with steam and oxygen.

* * * * *